United States Patent [19]
Bader

[11] Patent Number: 5,658,797
[45] Date of Patent: Aug. 19, 1997

[54] DEVICE FOR THE TREATMENT OF CELL CULTURES

[76] Inventor: Augustinus Bader, Hinter den Langen Hoefen 16, D-31275 Lehrte, Germany

[21] Appl. No.: 295,732
[22] PCT Filed: Mar. 2, 1993
[86] PCT No.: PCT/EP93/00468
§ 371 Date: Nov. 28, 1994
§ 102(e) Date: Nov. 28, 1994
[87] PCT Pub. No.: WO93/18133
PCT Pub. Date: Sep. 16, 1993

[30] Foreign Application Priority Data
Mar. 3, 1992 [DE] Germany ............ 42 06 585.2

[51] Int. Cl.⁶ ............................................ C12M 3/00
[52] U.S. Cl. .................... 435/284.1; 435/297.1; 435/297.2; 435/297.5; 435/307.1
[58] Field of Search ................... 435/284, 285, 435/301, 310, 284.1, 297.1, 297.2, 297.5, 305.1, 305.2, 307.1

[56] References Cited

U.S. PATENT DOCUMENTS

| | | | |
|---|---|---|---|
| 3,948,732 | 4/1976 | Haddad et al. | 435/285 |
| 4,201,845 | 5/1980 | Feder et al. | 435/285 |
| 4,225,671 | 9/1980 | Puchinger et al. | 435/71 |
| 4,661,455 | 4/1987 | Hubbard | 435/240 |
| 4,661,458 | 4/1987 | Berry et al. | 435/284 |
| 4,748,124 | 5/1988 | Volger | 435/240.241 |
| 5,316,945 | 5/1994 | Minuth | 435/285 |

FOREIGN PATENT DOCUMENTS

| | | |
|---|---|---|
| 0 180 165 | 5/1986 | European Pat. Off. . |
| 0 232 975 | 8/1987 | European Pat. Off. . |
| 0 363 262 | 4/1990 | European Pat. Off. . |
| 0 396 138 | 11/1990 | European Pat. Off. . |
| 0 416 586 A1 | 3/1991 | European Pat. Off. . |
| WO8911529 | 11/1989 | WIPO . |
| WO89/12676 | 12/1989 | WIPO . |
| WO90/12604 | 11/1990 | WIPO . |

*Primary Examiner*—David A. Redding
*Attorney, Agent, or Firm*—Michael B. McMurry; Kathleen Anne Ryan

[57] ABSTRACT

A device for treating cell cultures, especially hepatocytes, on plate-like culture slides, at least a part of the surfaces of the slides is gas permeable with oxygen being introduced inside of the slides. On the culture slide is applied a coating of collagen (5,7) on or in which is the cell culture (6). The next cell culture slide (1) is arranged closely above the collagen coating (5,7). The culture medium can be introduced into the space between the collagen coating (5,7) and the next culture slide (1).

25 Claims, 4 Drawing Sheets

DEVICE FOR THE TREATMENT OF CELL CULTURES

FIELD OF THE INVENTION

The invention relates to a device for the treatment of cell cultures, in particular liver cells (hepatocytes), on cell culture slides, at least a part of the surfaces of the cell culture slides being gas-permeable.

BACKGROUND OF THE INVENTION

In medicine and in the pharmacy it is often necessary to perform experiments with cell cultures. This applies, for example, to their culture, to their observation, their reaction on foreign and/or poisonous substances, to preservation and similar.

Furthermore the search for suitable organ replacements is becoming increasingly important.

One of the main areas is experiments regarding metabolic functions, especially of the liver.

The complexity of the large number of hepatocellular metabolic functions however places high demands on an artificial organ replacement for the liver. In the case of the artificial kidney, filtration and metabolic functions, which can be performed by equipment in the manner of dialysis, are of prime importance. Similarly with an artificial heart the pumping function in particular is replaced by a machine. The liver on the other hand has a large number of individual functions, which can be roughly divided into categories such as detoxifying function, protein secretion, endocrine functions, storage function, phagocytosis, fat and carbohydrate metabolism functions.

In known culture systems the liver cells, i.e. the hepatocytes, loose their functional ability within the first few days after isolation. Thus after just 2 to 3 days, depending on the function investigated, only roughly 80% and after 1 week only minimal residual functions remain. Later on cell death and proliferation with fibroblast-type cells occur. Previous experiments with liver cell cultures had to be performed in a phase with progressive cell degeneration.

To obtain the hepatocyte function in culture it has, for example, already been proposed practising epithelial co-culture, the addition of dimethylsulphoxide (DMSO) to the medium, or the use of a complex matrix (matrigel). However if the objective is the use of a liver cell culture which is to imitate as closely as possible the "in vivo" situation, a series of problems is produced by these conventional culture methods. Thus DMSO is a chemical substance also having a hepatotoxic action. Epithelial co-cultures are transformed cell lines and have an oncogenic character. It is therefore not possible to draw conclusions on the behaviour of naturally completely differentiated cells. Matrigel is in turn derived from sarcoma cell lines (Engelbrecht Holm sarcoma) and is not characterised in its components. A clinical use of oncogenic cells or their products (not defined in further detail) is therefore not worth striving for.

A system has already been proposed which generally consists of a hepatocyte monolayer with adhesion on one side to glass, plastic, or extracellular matrix containing protein as the cell culture slide.

A so-called sandwich culture system having a matrix-hepatocyte-matrix structure is also known. However for performance this system requires a surface as a support which has to be accessible for the application of the second upper layer. Devices on a base of hollow fibres or microcarriers in fact theoretically enable a mass culture, but are always used with conventional culture configurations. This causes a fast functional loss of the hepatocytes, and in addition significant oxygenation problems occur. A sandwich culture system can not be achieved in this manner, as adhesions would ensue.

A further disadvantage of the known cultures, especially of sandwich cultures, lies in that the oxygen supply to the cells could not adequately be ensured. In some regions there was under-supply, whereas in other regions there occurred an increase in the perfusion speed of the culture medium resulting in unwanted increases in transverse forces.

In order to avoid such oxygenation problems of cell structures, especially of hepatocytes in culture, gas-permeable membranes have already been proposed. In this case the cells, which lie on one side of the membrane, are supplied either by transmembrane air contact or via oxygen-enriched medium, which flows past the opposite side. However such individual membranes are only suitable for laboratory purposes or only for small quantities and sizes respectively.

A further main disadvantage of the known methods and structures lies in spatial problems, i.e. their large space requirement. Thus the removal of oxygenation and nutrient supply problems, for example, requires expensive separate pump circuits, which results in an enormous increase in size of the unit in relation to the number of cells actually cultivated. A mass culture is not possible in this manner, as a total organ replacement, e.g. of a human liver, with such a technology would have the spatial requirement of an entire house.

From EP 0 363 262 a device is known for the treatment of cell cultures using a three-chamber system inside a basic unit having a fixed housing. Two individual membranes separated from one another extend in this housing, as a result of which three chambers are produced. These membranes are separately attached in the walls of the basic unit. The cell culture space is in the central chamber, while the two other chambers represent supply chambers for the cell culture chambers.

However, a disadvantage is that, even with this device, the spatial requirement is considerable. Furthermore with this device it is not possible to achieve at least roughly an "in vivo" state for the cells.

SUMMARY OF THE INVENTION

The object of the present invention is therefore to create a device of the type mentioned at the beginning, with which a mass culture is possible under sensible spacial conditions and in a state which comes as close as possible to an "in vivo" state.

This object is achieved in accordance with the invention in that oxygen can be introduced inside the plate-like cell culture slides, and in that a collagen layer covering the cells is applied to the cell culture slide, the next cell culture slide being disposed directly or at a slight distance above the collagen layer and it being possible to introduce culture medium (into) the collagen layer or into the space between the collagen layer and the next cell culture.

The construction principle according to the invention in the form of a bioreactor enables an arrangement for the treatment of cell cultures to be created in the smallest space, with which a substantially larger number of cells can be cultivated than in known solutions. By the design of the cell culture slides according to the invention a sufficient and substantially uniform oxygen supply of the cell culture is created.

The construction principle of the bioreactor in accordance with the invention imitates the microanalytical and functional unit of the liver parenchyma, the liver lobule. With a separate arterial and portal venous—venous phase this simultaneously enables several important advantages when compared with known systems and methods. Thus for example an optimal, i.e. direct, precisely metered and uniformly distributed supply of the hepatocytes with oxygen is possible. Furthermore the overall cell number can be adapted to requirements (mass culture) so that it is as high as required. The dead volume of the bioreactor can be kept to a minimum.

If in a very advantageous refinement of the invention it is specified that the cell culture is disposed on a first collagen layer, and that a second, upper collagen layer lies over the cell culture, then the hepatocytes are immobilised in a collagen sandwich, as a result of which an even better "in vivo" type morphology and function of the cells is achieved.

A further very advantageous refinement of the invention lies in that, because of the design of the bioreactor specified by the invention, it is also possible to treat, apart from the first cell culture, a second cell culture, e.g. non-parenchymal cells. In this manner a co-cultivation in ordered three-dimensional structures is made possible, such as, for example, sinusoid—matrix—hepatocyte—matrix—non-parenchymal cell—sinusoid . . . . Here the first sinusoid represents the oxygen supply chamber in the cell culture slide, while the second sinusoid is formed by the space between the upper collagen layer and the next cell culture slide or the next cell culture layer respectively.

If the bioreactor according to the invention is used for example for the cultivation of hepatocytes, the cell culture slide represents a cross section through a liver lobule. The liver cells (hepatocytes) are attached in confluent layers inside the collagen matrix, consisting of a lower and upper collagen layer, similar to Disse's space. Capillary spaces, which correspond to the sinusoids, are located above and below the stackable cell layers. These transport portal-venous nutrient medium as culture medium and, in a separate arterial phase, oxygen through the interior of the cell culture slides. The supply is performed via portal fields at the periphery of the cell culture slide. Oxygen also overflows into the portal-venous phase and flows therewith into the venous phase, which is formed by the space. Similarly to the central vein, the nutrient medium is collected and carried away by all cell culture slides which imitate the lobules or spaces respectively.

The nutrient medium from all spaces can be collected in a basin and be returned via a pump, e.g. a peristaltic pump, in the circulation to the bioreactor. If necessary, substances can be separated from the circulation by an interposed filter appliance. This applies, for example, to bile, if the culture medium is not changed now and then.

The cell culture slides can be manufactured from a variety of materials. The important thing is just that they are bilaminar, i.e. at least their large, opposite surfaces are gas-permeable, but not liquid-permeable. If necessary the surfaces may however also be semi-permeable or fluid-permeable. In such a case an exchange of substances can occur through the cell culture slides.

In a simple design it can be specified that the cell culture slide is formed from an upper and a lower sintered metal strip, which are separated from one another by spacers. Then oxygen or air with carbon dioxide respectively is introduced between the two strips. Depending on the number and type of the cell culture slides, normal atmospheric pressure or slight excess pressure may be sufficient to ensure that oxygen diffuses through the gas-permeable layer, and thus enters the adjacent collagen layer.

Such cell culture slides have a high mechanical stability.

Instead of sintered metal, plastics which are correspondingly gas-permeable are also suitable as material for cell culture slides. Polypropylene and silicon films, which have the additional advantage that they are transparent, are suitable for this. In this way it is possible to observe the cells with a light-optical microscope.

The design of the bioreactor specified by the invention guarantees a largely uniform distribution of the oxygen supply, as each cell has its own oxygen space. In addition the oxygen supply is exactly tailored to requirements by metering and is independent of internal conditions relating to flow technology.

To meet the requirements the required total cell number can be adapted to any level in a very simple manner by layering any number of cell cultures slides via a common oxygen supply (module method). The spaces conveying the culture medium are separated from the cell culture slides and their oxygen supply by sealing rings.

The significance of this direct oxygenation by means of bilaminar membranes and their stacking mode becomes clear if one bears in mind that in this way for the first time even large cell units can be supplied uniformly with oxygen in three-dimensional structures in the smallest space. The spacing of the plates is regulated via the sealing rings, e.g. elastic silicon sealing rings, which act both as spacers and also as separating agents between the fluid phase (venous) and gas phase (arterial). By choosing the size and diameter of the sealing rings, the spacing between the plates can be regulated as desired. If necessary a capillary gap can remain between the plates and thus a "sinusoid" is created. A further advantage here is that the spacing can be minimised and thus dead volumes are avoided.

Instead of manufacturing the plate-shaped cell culture slides from sintered metal, they can if necessary also be formed completely from a non-toxic plastic, in which case a transparent plastic is preferably used for this, as in this case it is possible to simply observe the culture.

A possible embodiment for this may lie in that the cell culture slides are formed from a supporting frame, on or over which a gas-permeable membrane is stretched.

The supporting frame may consist of an outer annular member and an inner annular member surrounding the central bore, both annular members being connected to one another by spoke-shaped ribs.

This design is very simple to produce, and a sufficiently great stability for the supporting frame is provided, so that if necessary the cell culture slides can be produced with a thickness of less than 1 mm. The gas-permeable membrane may be, for example, a Teflon film, having a thickness of 0.0025 mm.

The supply apertures for oxygen will advantageously be disposed in at least a part of the ribs, and air ducts are disposed in the ribs. The air ducts ensure the distribution of the supplied oxygen inside the cell culture slide.

With a hepatocyte cultivation according to the invention a stable function has so far been achieved within 7 weeks, for example. Cell layers lying between the plates can be completely and adequately oxygenated from two sides. This enables the three-dimensional reconstruction of a normal liver architecture: sinusoid—matrix—hepatocyte—matrix—non-parenchymal cell—sinusoid etc. without ischaemic problems. A free gas exchange with the arterial and portal venous—venous phase is produced over the cell layers.

As an alternative to the sequence given above, if necessary a complete double unit may also be provided on the upper side of a cell culture slide. In such a case the layer structure on the upper side of a cell culture slide occurs in the following sequence: first collagen layer—cell culture—second collagen layer—cell culture—third collagen layer. Then the next cell culture slide is placed on top of the third, i.e. the upper collagen layer. During assembly it should just be ensured that a space is left between the third, upper collagen layer and the under side of the cell culture slide placed on top. Then the culture medium is introduced into this space. Therefore in such a case a fourth collagen layer is dispensed with, as the middle collagen layer outwardly seals both cell cultures. In fact the supply of culture medium does not occur centrally between the two middle collagen layers, but as the collagen layers can be permeated without any problem by the culture medium, in this case too an adequate supply is provided for the lower cell culture.

The supply of gas or oxygen respectively to the bilaminar cell culture slides can be performed at the periphery of the cell culture corresponding to the arterial supply in the portal field of a liver lobule. The cell culture slides can be located in a glass jar as a housing. Culture medium can also be added peripherally and from below (portal-venous intake) and is then distributed in ascending fashion at the circumference of the plates and flows above and below each individual bilaminar cell culture slide to a central aperture. An upwardly tapering cone, for example, is located there. This results in an upwardly directed lumen accretion or increase in the clear width of the space of the "central vein" and in the absence of unnecessary dead volume enables the culture medium to flow away in a controlled manner from the perimeter to the centre and then upwardly. The bioreactor then empties at the top and medially (venous phase). When the cell layers overflow, the transfer from the portal-venous and arterial phase into the venous phase has been completed. This corresponds to the "in vivo" organisation of the liver.

The bioreactor according to the invention has many different possible applications in medicine and in the pharmacy.

One of its main uses is as an artificial liver or as a liver replacement respectively.

The metabolism of a large number of drugs occurs in the liver. Lipophile drugs, such as for example ciclosporin or FK 506 are metabolised in species-dependent manner to produce various kinds of metabolites. These metabolites are partially responsible for the action of the substance but also for its toxicity. Not until clinical testing was it possible to demonstrate the different metabolite specimen and its toxicity in the human being in contrast to the animal experiment.

The development of a dynamic human system, but without humans, would have fundamental advantages in comparison with experiments on animals before the beginning of a clinical test with regard to the validity of the results. In the ethical respect as well the question is raised of whether, because of the unsafe animal experiments, the first-time testing, especially of high active substance concentrations of lipophile medicaments in human beings, can still be advocated within the framework of clinical testing.

Furthermore in experiments on large animals and primates the development of a temporary organ replacement by means of the animal's liver has been striven for. Cross perfusion with a pavian liver is already clinically used with varying success.

In accordance with the invention the pulsatile properties of the bioreactor circulation can be exploited and metabolites of drugs can be detected. Medicaments and hormones reach the liver in an "in vivo" pulsatile state.

These conditions can be simulated by the bioreactor. Peak and through values of a mother substance and also their metabolites can be determined. First pass and recirculating studies are possible. Furthermore metabolite specimens in animal and human cells can be determined. An investigation of the direct toxicity, especially with high doses, is also possible.

Furthermore the controlled determination of a dose-related kinetics of metabolite development can be performed. Previously such a situation could only be investigated in animal experiments.

There are physiological differences in the behaviour between human and rat hepatocytes. Animal experiments as such are subject to these restrictions.

The number of animals used for pharmacokinetic and metabolic experiments in industry is very high, as these are almost exclusively performed on laboratory animals. For reasons of transferability to humans, one of 2 animal types must be similar to the human being in metabolic behaviour. However this can vary depending on the substance used. A suitable type of animal can therefore only be predicted with reservations. Of course the stress depends on the substance used.

With the use of the bioreactor specified by the invention, if necessary such experiments can now be discontinued to a large extent. Thus, for example, human hepatocytes from surgical specimens after liver resection or from non-transplanted or only partly transplanted organs are available and can be used in the bioreactor specified by the invention.

Liver diseases, which may result in the total failure of the organ, are common and can occur in any human being in an acute and unexpected manner. These include hepatitis and also liver tumours, and also liver damage caused by poisons (death-head poisoning, alcohol), and also accidents.

Artificial organ replacement by the bioreactor according to the invention pursues two objectives:

1. The waiting time between the onset of liver failure and the availability of a new organ in the event of a planned liver transplant is to be bridged. Patients often die in this waiting period.

2. Liver failure does not always have to be final. If a patient in such a situation were given the possibility of a supportive treatment by a organ replacement from another quarter, the patient could in some circumstances survive such a situation. His own liver would have time to regenerate. This is especially possible in the event of acutely traumatic or toxic damage to the liver. However even with extensive tumour operations the reserve of a temporary organ replacement can reduce the operation risk or enable greater intervention. The body itself produces a large quantity of growth factors which enable a regrowth of the remaining, healthy residual liver.

Previous treatment methods include the removal of metabolic toxins and a filtration of the blood. Unfortunately the growth factors are removed at the same time and healing is prevented.

A further possible use of the bioreactor according to the invention lies in the large-scale production of coagulation factors, such as e.g. liver synthesis products. Previously coagulation factors were obtained from human blood taken from blood donors. However in this case there is the risk of a hepatitis contamination or an Aids infection. With the bioreactor specified by the invention, coagulation factors, for example, can now be obtained free from infection without blood donors having to be used. This is an alternative solution to the expensive genetic method of obtaining of liver synthesis products.

BRIEF DESCRIPTION OF THE INVENTION

An exemplified embodiment of the invention is represented in principle by means of the drawings.

DETAILED DESCRIPTION

A plurality of cell culture slides 1 disposed with a spacing between them and one above the other, which are constructed as silicon-coated plates made from sintered metal, form the core of the bioreactor.

Figure 1:
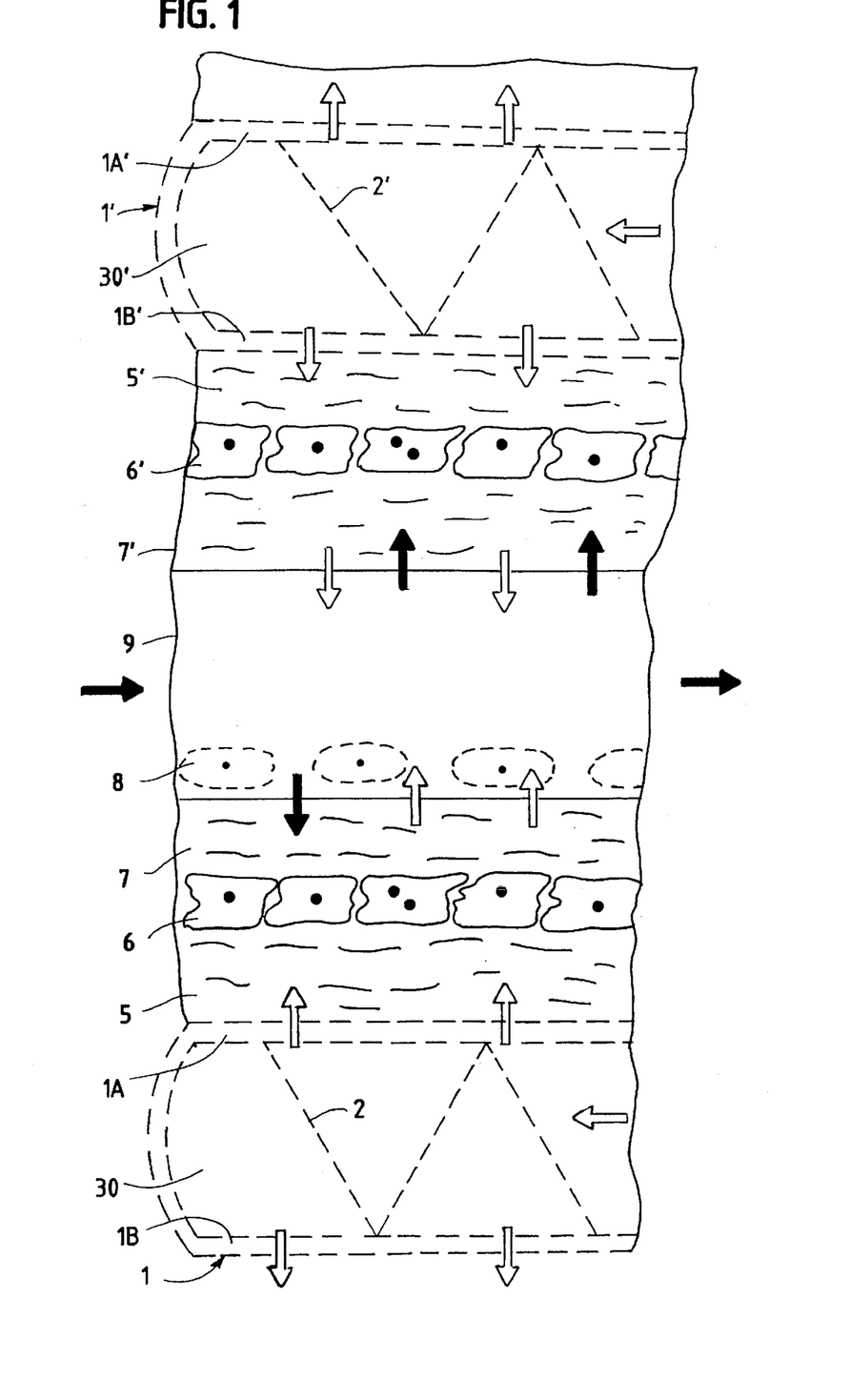
FIG. 1 shows a diagrammatical representation of the principle of construction of the bioreactor in detail.
Figure 3:
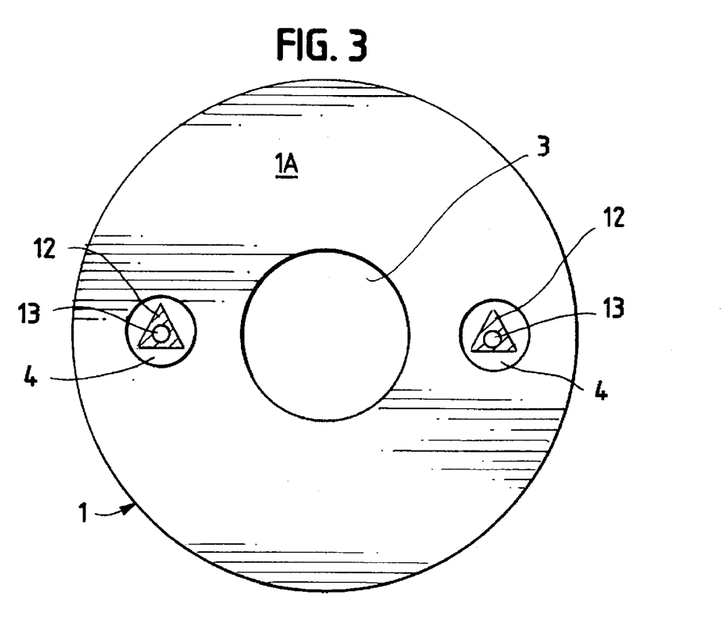
FIG. 3 shows a top plan view of a cell culture slide plate.

As can be seen in the large representation in FIG. 1, each cell culture slide or plate 1 includes two gas permeable surfaces 1A and 1B that are separated from each other by spacers 2 to form a free interior space 30 within the plate 1. The upper and lowers surfaces 1A and 1B can be conveniently formed by a thin surface coating, such as a sintered metal or plastic strip, which is supported by the spacers 2 to form the first surface 1A and is bent over and around the spacers 2 to form the second gas permeable surface 2A. As can be seen from FIG. 3, each plate 1 is provided with a central aperture 3. the bores 4 being located between the outer periphery and the central aperture 3. The bores 4 are used for the supply of oxygen into the interior of the plates 1. For this reason the bores 4 should be provided in such a distribution in each plate 1 that a sufficient and uniform distribution of oxygen can occur.

A first hydrated collagen layer 5 (e.g. protein from skin, bone and cartilage) is applied in a thickness of roughly 0.5 mm onto the upper side of the upper strip 1A. A cell culture layer 6, e.g. hepatocytes, follows on this collagen layer 5. A second, upper collagen layer 7 is applied to the cell culture layer 6. If necessary a further layer of e.g. non-parenchymal cells 8 can be applied on top (see representation in broken lines in FIG. 1). The two collagen layers 5 and 7 do not represent any fundamental barrier for the supply of gas or air respectively and the diffusion of nutrients to the hepatocytes. Even large molecules can pass through this layer without any problems. As the cells 6 directly lie on the cell culture slide 1 as an oxygen carrier by means of the first collagen layer 5, as a result, with respect to the gas diffusion, a situation as in an incubator after the removal of the medium is produced. This is the prerequisite for the optimisation of an oxygen supply in the cultivation of large cell numbers in confluent layers. However in the bioreactor the nutrient-carrying culture medium is not omitted. This is supplied via the small distance or space between the upper collagen layer 7 and a further supporting unit. The further (and following) supporting unit in turn consists of a lower or inner collagen layer 5', which is applied to the further cell culture slide 1' with corresponding upper gas permeable surface (1A'), lower gas permeable surface (1B'), which are separated by spacer 2', the slide 1' being mounted at a distance above the first cell culture slide 1. In turn the cell culture layer 6', which is covered on the outside by the second or outer collagen layer 7', follows on the inner collagen layer 5'. In practice this unit is upended and its supply with nutrients or plasma, for example, is performed via the common space 9.

In a modification of the design represented in FIG. 1, the double unit represented having two layers of cell cultures 6 and 6', which is disposed between two cell culture slides 1 and 1' respectively, can also be completely constructed starting from the upper side of the lower cell culture slide 1. This method is recommended particularly when there is a danger that the collagen layer 5' does not adhere or only poorly adheres to the under side of the cell culture slide 1' disposed over it. Furthermore the work on or the structure of the bioreactor respectively is facilitated if necessary.

In this case the upper cell culture 6' is laid directly on the upper collagen layer 7 instead of on the space 9, as represented by the non-parenchymal cell culture layer 8. Then the upper collagen layer 5' is applied on the upper cell culture layer 6' and subsequently the next cell culture slide 1' is placed on top. In this case care just has to be taken so that during the assembly between the upper collagen layer 5' and the under side of the cell culture slide 1' a small space remains for the supply of culture medium. Therefore in this case the supply of nutrients to cell culture layers 6 and 6' is performed from above through the collagen layer 5'. Collagen layer 7' is omitted and now there is a central collagen layer 7.

As can be seen, the oxygen requirement of metabolically active hepatocytes is guaranteed independently of the medium and the rate of flow of the medium. The cell culture slides 1 themselves represent the oxygenator, as a result of which confluent cell layers 6 can also be supplied with precisely metered quantities of oxygen by using the capillary network.

Figure 2:
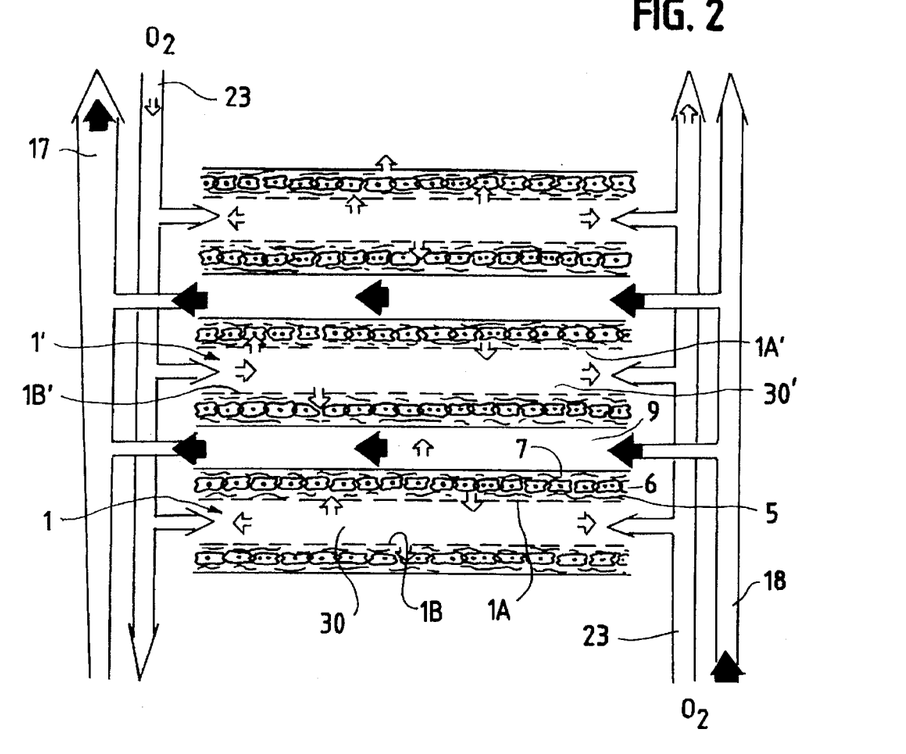
FIG. 2 shows a basic representation of the mode of operation of the bioreactor.

In FIG. 2 the structure of the bioreactor is represented diagrammatically. Here the black arrows indicate the path and flow direction of the culture medium, while the white arrows represent the course of the oxygen. The same also applies for the remaining arrows represented in FIGS. 1 and 4.

In this case oxygen is introduced via a common oxygen line 23, which is explained in further detail in connection with FIG. 4. Culture medium is also supplied in uniform distribution to all spaces 9 via a common line 18.

Figure 4:
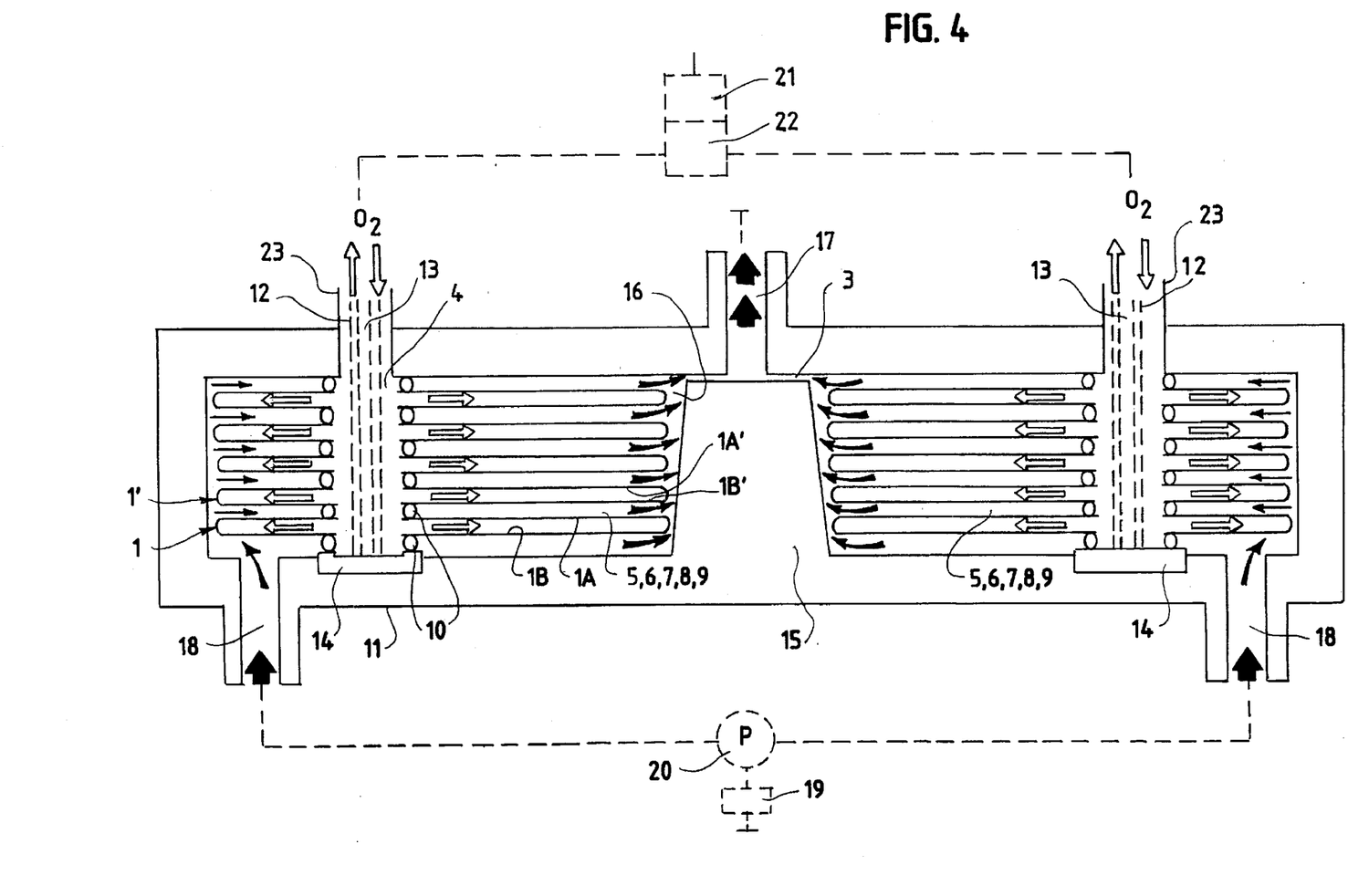
FIG. 4 shows an overall view of the bioreactor according to the invention.

The overall construction of the bioreactor can be seen from FIG. 4. As represented, a plurality of cell culture slides 1 is disposed spaced apart one on top of the other, with sealing rings in the form of silicon sealing rings 10, which are laid around the oxygen bores 4 of each plate, ensuring both that a distance is kept between the plates 1 and that there is a seal between the fluid phase (venous) and the gas phase (arterial). The choice of size or thickness respectively of the silicon sealing rings 10, which are compressed when the plates are assembled, ensures that a capillary space 9 remains between the plates and thus form the "sinusoid".

The supply of oxygen into the housing 11 of the bioreactor is performed via an oxygen line 23 into the oxygen bores 4, lying above one another in alignment, of the cell culture slides 1. A rod 12, which is triangular when viewed in cross section, is used to connect the cell culture slides 1 to one another. In this manner sufficient free space for the introduction of oxygen remains between the bore walls of the oxygen bores 4 and the rod 12 (see FIG. 3). The rod 12 is provided with a central bore 13, through which a straining screw is placed, which together with a lock nut or lock plate 14 respectively on the under side ensures a connection and gas-tight bracing of the silicon sealing rings 10 in a manner no longer represented. A cone, e.g. a glass cone 15, is inserted into the free space which is produced by the central apertures 3 of the cell culture slides 1 which lie in alignment one above the other. The glass cone 15 has a smaller diameter than the diameter of the central apertures 3, as a result of which a space 16 is created. As the cone 15 upwardly tapers, the space 16 becomes larger in this manner, as a result of which a good and uniform discharge of the culture medium via a common outlet line 17 is ensured.

As can be seen, the culture medium flows at both sides of the bioreactor via inlet lines 18 into the housing 11 and from there peripherally along the space 9 in the inward direction, where it flows away via the space 16.

The culture medium can be circulated, in which case a collecting basin 19 and a following pump 20 is provided, which conveys the culture medium again to the inlet lines 18 via the line shown by broken lines. If necessary a filter device for separating unwanted constituents from the culture medium occurring from the bioreactor can also be provided in the circulating line.

If the bioreactor is not disposed in an incubator, the oxygen, which can be mixed with roughly 5% carbon dioxide, is generally supplied via a preheater 21 and a humidifier 22 to the bioreactor. The air leaving the bioreactor can be passed through a water column. In this manner a carbon dioxide exchange with the surrounding air is prevented, as a result of which the desired high carbon dioxide content can in practice be stabilised in a type of closed system.

Figure 5:
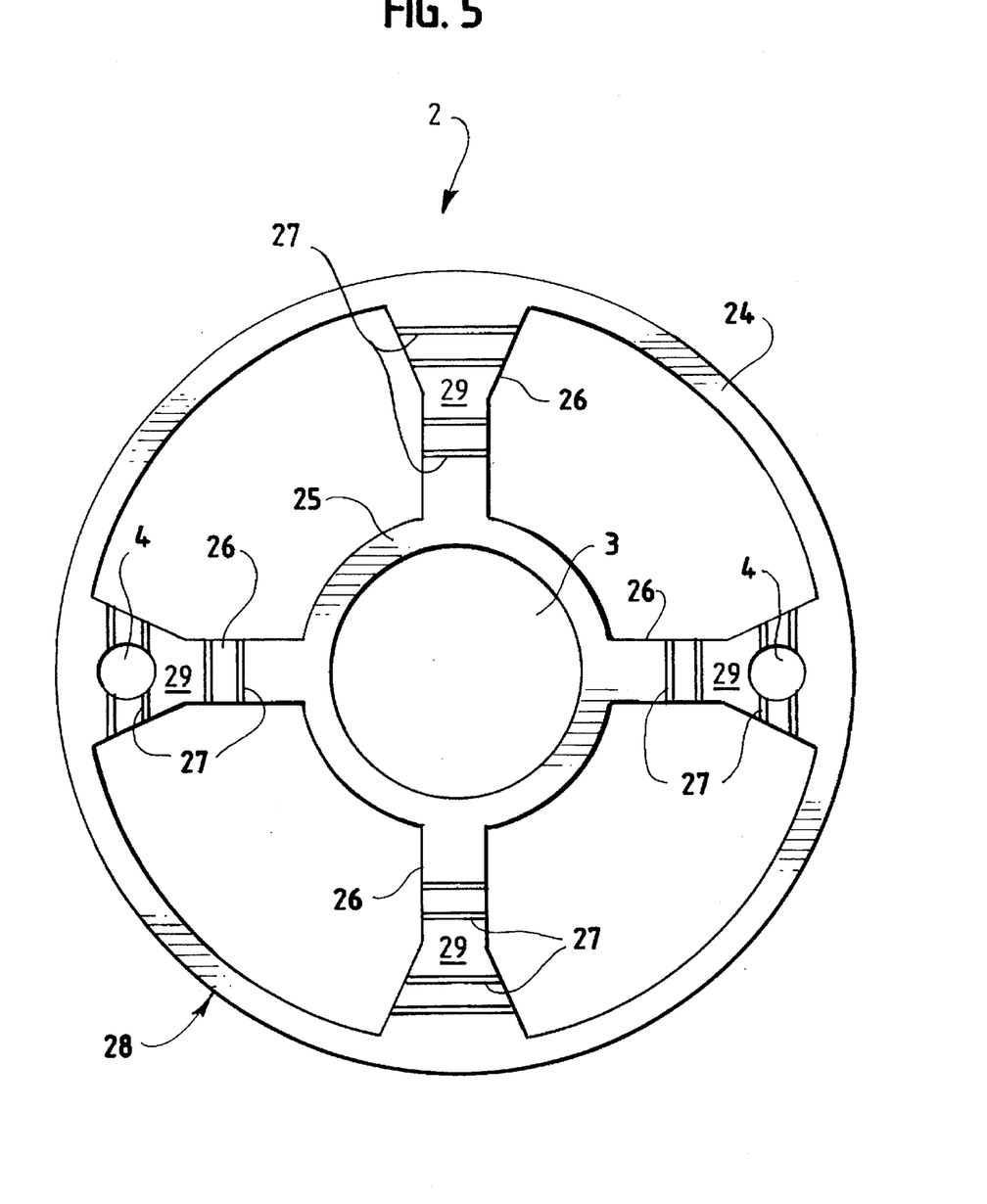
FIG. 5 shows a top plan view of spacers that can be used to support gas permeable membranes which form part of a cell culture slide.

FIG. 5 depicts a top plan view of the upper side 28 of a spacer 2 according to the invention. An outer annular member 24 and an inner annular member 25, which surrounds the central bore 3, are used as a supporting frame for the spacer 2. The spacer 2 preferably is made of a non-toxic plastic. The spacer 2 further includes spoke-shaped ribs 26 which connect the outer annular member 24 and the inner annular member 25. The supply apertures 4 for oxygen are disposed in two opposite ribs 26. To complete the construction of the plate 1 (not shown) in accordance with the invention, a gas permeable membrane, such as a Teflon film, is stretched over the upper side 28 and lower side (not shown) of the spacer 2 to form the gas permeable surfaces, 1A and 1B (not shown), respectively. So that the oxygen is distributed uniformly inside the cell culture slide 1, each rib 26 of the spacer 2 is provided with one or more air ducts 27 on the upper surface 29 of the rib 26 and on the lower surface (not shown) of the rib 26. The air ducts 27 pass through the width of the ribs 26.

The thickness or spacings respectively of the individual layers are to be selected in dependence on the cell cultures to be treated. For the cultivation of hepatocytes thicknesses of roughly 0.5 mm for the cell culture slides 1 have proved to be very suitable, and the gas-permeable surface layer or the sintered strip respectively may be only 0.1 mm or less if necessary. For the two collagen layers thicknesses of 0.4 to 0.6 mm, preferably 0.5 mm, have proved to be suitable. The cell culture layer may have a thickness of 0.002 to 0.003 mm. A few tenths of millimeters suffice for the space 9.

If it is estimated that the hepatocyte content of 1 g liver is 100 million, then the liver of a 250 g rat weighing 8 to 10 g would contain 800 million to 1 thousand million hepatocytes. Experiments have shown that this is sufficient for a capacity of a bioreactor having an internal height of roughly 30 mm and a diameter of the plate-shaped cell culture slides of roughly 10 to 15 cm.

So that it is possible to take over the functions of a human liver, or as an artificial human liver respectively, it is estimated that roughly 2,000 plates lying one on top of the other would be necessary, which with the plates arranged in 4 columns, e.g. in a clover-leaf structure, would produce an overall height of roughly 80 to 100 cm. The volume requirement of the bioreactor for culture medium would be relatively low at roughly 10 l. The metabolic process with the patient's plasma could occur via a basin.

I claim:

1. A device for treating a mass cell culture, especially hepatocytes, comprising:
    a first flat cell culture slide having a first surface which is at least partially gas permeable and a second surface spaced apart from said first surface to form an interior, said second surface being at least partially gas permeable, wherein a portion of the mass cell culture is applied to said first surface;
    a first collagen layer applied to said first surface of said first cell culture slide and at least partially enveloping said portion of the mass cell culture;
    a second flat cell culture slide having a first surface which is at least partially gas permeable and a second surface spaced apart from said first surface to form an interior, said second surface being at least partially gas permeable, said second cell culture slide being spaced apart from said first cell culture slide to form a space between said first collagen layer and said second cell culture slide;
    oxygen delivery means for delivering oxygen into said interior of said first culture slide and into said interior of said second cell culture slide; and
    nutrient delivery means for delivering nutrients to said portion of the mass cell culture.

2. The device of claim 1 wherein said nutrient delivery means is in fluid communication with said space.

3. The device of claim 1 further comprising a second collagen layer applied to said first cell culture slide intermediate said portion of the mass cell culture and said first surface.

4. The device of claim 3 wherein said nutrient delivery means is in fluid communication with said space.

5. The device of claim 1 further comprising a second cell culture disposed on said first collagen layer.

6. The device of claim 5 wherein said second cell culture comprises non-parenchymal cells.

7. The device of claim 1 wherein said first and second cell culture slides are formed from sintered metal.

8. The device of claim 1 wherein said first and second surfaces of said first cell culture slide and said first and second surfaces of said second cell culture slide are formed from sintered metal.

9. The device of claim 1 wherein said first and second cell culture slides are formed from a gas-permeable plastic.

10. The device of claim 1 wherein said first and second surfaces of said first cell culture slide and said first and second surfaces of said second cell culture slide comprise a gas-permeable membrane.

11. The device of claim 10 wherein each of said first and second cell culture slides further comprise a plurality of spacers located between said first and second surfaces, said plurality of spacers including an outer annular member, an inner annular member, and a plurality of spoke-shaped ribs, said inner annular member being spaced apart from said outer annular member and surrounding a central bore, said outer annular member being connected to said inner annular member by said plurality of spoke-shaped ribs.

12. The device of claim 11 wherein said spoke-shaped ribs include air ducts and wherein at least a portion of said spoke-shaped ribs further include oxygen-supply apertures.

13. The device of claim 1 wherein said first and second surfaces of said first cell culture slide and said first and second surfaces of said second cell culture slide are formed from a material selected from the group consisting of silicon film and polypropylene film.

14. The device of claim 1 further comprising sealing rings interposed between said first and second cell culture slides.

15. The device of claim 1 further comprising a third flat cell culture slide spaced apart from said second cell culture slide and positioned so that said second cell culture slide is intermediate said first and third cell culture slides, and a housing for containing said first, second, and third cell culture slides to form a first unit, wherein said oxygen supply means comprises at least one oxygen supply line and said nutrient supply means comprises at least one nutrient inlet line for delivering nutrients and at least one nutrient outlet line for receiving nutrient discharges.

16. The device of claim 15 wherein each of said fist, second, and third cell culture slides is substantially disk-shaped and has a centrally-located aperture, wherein said nutrient inlet line delivers nutrients to the peripheries of said first, second, and third cell culture slides, wherein said nutrient outlet line receives the nutrient discharge from said centrally-located apertures of each of said first, second, and third cell culture slides, and wherein each of said first, second, and third cell culture slides further comprises at least two oxygen supply apertures for disposing oxygen uniformly over the circumference of each of said slides.

17. The device of claim 16 further comprising a discharge cone, said cone being disposed through said centrally-located aperture of each of said first, second, and third cell culture plates and having an outside diameter less than the diameter of said centrally located apertures.

18. The device of claim 16 further comprising a tensioning device extending through said oxygen supply apertures.

19. The device of claim 18 wherein each of said oxygen supply apertures has a substantially circular cross-section and wherein said tensioning device comprises a non-circular guide rod having a hollow interior and a straining screw positioned within said interior.

20. The device of claim 15 further comprising four, fifth, sixth, seventh, eighth, ninth, tenth, eleventh, and twelfth cell culture slides, said fifth cell culture slide being positioned intermediate said forth and sixth cell culture slides to form a second unit, said eighth cell culture slide being positioned intermediate said seventh and ninth cell culture slides to form a third unit, and said eleventh cell culture slide being positioned intermediate said tenth and twelfth cell culture slides to form a fourth unit, said first, second, third, and fourth units arranged in a clover-leaf fashion.

21. The device of claim 1 in which the nutrient supply means comprises a pump for delivering the nutrient and a basin for collecting a nutrient discharge from said portion of the mass cell culture.

22. The device of claim 21 wherein said nutrient supply means further comprising a filter device for filtering the nutrient discharge.

23. A device for treating a mass cell culture, especially hepatocytes, comprising:
   a first module comprising;
      a first flat cell culture slide having an upper surface which is at least partially gas permeable and a lower surface spaced apart from said upper surface to form an interior, said lower surface being at least partially gas permeable, wherein a first portion of the mass cell culture is applied to said upper surface of said first flat cell culture slide;
      a first collagen layer applied to said upper surface of said first cell culture slide and at least partially enveloping said first portion of the mass cell culture;
      a second flat cell culture slide having an upper surface which is at least partially gas permeable and a lower surface spaced apart from said upper surface to form an interior, said lower surface being at least partially gas permeable, said second cell culture slide being spaced apart from said first cell culture slide to form a space between said first collagen layer and said second cell culture slide, wherein a second portion of the mass cell culture is applied to said upper surface of said second flat cell culture slide;
   a second module comprising;
      a second collagen layer applied to said upper surface of said second cell culture slide and at least partially enveloping said second portion of the mass cell culture;
      a third flat cell culture slide having an upper surface which is at least partially gas permeable and a lower surface spaced apart from said upper surface to form an interior, said lower surface being at least partially gas permeable, said third cell culture slide being spaced apart from said second cell culture slide to form a space between said second collagen layer and said third cell culture slide;
   oxygen delivery means for delivering oxygen into said interior of said first culture slide, into said interior of said second cell culture slide, and into said interior of said third cell culture slide; and
   nutrient delivery means for delivering nutrients to said portion of the mass cell culture.

24. The device of claim 23 wherein said nutrient delivery system is in fluid communication with said space between said first collagen layer and said second cell culture slide, and with said space between said second collagen layer and said third cell culture slide.

25. A device for treating a mass cell culture, especially hepatocytes, comprising:
   a first flat cell culture slide having an upper surface which is at least partially gas permeable and a lower surface spaced apart from said upper surface to form an interior, said lower surface being at least partially gas permeable;
   a first collagen layer applied to said upper surface of said first cell culture slide, wherein a first portion of the mass cell culture is applied to the first collagen layer;
   a second collagen layer applied to said first collagen layer and enveloping said first portion of the mass cell culture;
   a second flat cell culture slide having an upper surface which is at least partially gas permeable and a lower surface spaced apart from said upper surface to form an interior, said lower surface being at least partially gas permeable;
   a third collagen layer applied to said lower surface of said second cell culture slide, wherein a second portion of the mass cell culture is applied to said first collagen layer;
   a fourth collagen layer applied to said third collagen layer and enveloping said second portion of the mass cell culture, said second cell culture slide being spaced apart from said first cell culture slide to form a space between said second collagen layer and said fourth collagen layer;
   oxygen delivery means for delivering oxygen into said interior of said first culture slide and into said interior of said second cell culture slide; and
   nutrient delivery means for delivering nutrients to said first and second portions of the mass cell culture, said nutrient delivery means being in fluid communication with said space between said second collagen layer and said fourth collagen layer.

* * * * *